United States Patent [19]
Woloszko et al.

[11] Patent Number: 5,834,051
[45] Date of Patent: Nov. 10, 1998

[54] INTRAMUSCULAR STIMULATION LEAD WITH ENHANCED INFECTION RESISTANCE

[75] Inventors: Jean A. Woloszko, Jupille, Belgium; Marc Hendriks, Hoensbroek, Netherlands; Patrick T. Cahalan, Geleen, Netherlands; Michel L. P. M. Verhoeven, Maastricht, Netherlands; Linda L. Cahalan, Geleen, Netherlands; Antoine N. J. Camps, Eys Wittem, Netherlands

[73] Assignee: Medtronic, Inc., Minneapolis, Minn.

[21] Appl. No.: 801,986

[22] Filed: Feb. 19, 1997

Related U.S. Application Data

[62] Division of Ser. No. 553,206, Nov. 7, 1995.
[51] Int. Cl.⁶ .................. B05D 7/22; B05D 7/24
[52] U.S. Cl. .............. 427/2.24; 427/2.1; 427/118; 427/230
[58] Field of Search .................. 427/2.12, 2.13, 427/2.24, 409, 412.1, 2.1

[56] References Cited

U.S. PATENT DOCUMENTS

| | | | |
|---|---|---|---|
| 4,311,479 | 1/1982 | Fenn et al. | 8/495 |
| 4,539,234 | 9/1985 | Sakamoto et al. | 427/393.5 |
| 4,642,104 | 2/1987 | Sakamoto et al. | 604/264 |
| 4,677,143 | 6/1987 | Laurin et al. | 523/122 |
| 4,735,205 | 4/1988 | Chachques et al. | 128/419 PG |
| 4,810,567 | 3/1989 | Calcaterra et al. | 428/224 |
| 4,879,135 | 11/1989 | Greco et al. | 427/2.31 |
| 4,952,409 | 8/1990 | DeLeon et al. | 427/2 |
| 5,019,096 | 5/1991 | Fox, Jr. et al. | 623/1 |
| 5,086,787 | 2/1992 | Grandjean et al. | 128/786 |
| 5,103,837 | 4/1992 | Weidlich et al. | 128/784 |
| 5,176,916 | 1/1993 | Yamanaka et al. | 424/448 |
| 5,229,172 | 7/1993 | Cahalan et al. | 604/264 |
| 5,344,455 | 9/1994 | Keogh et al. | 623/1 |
| 5,423,876 | 6/1995 | Camps et al. | 607/116 |
| 5,425,751 | 6/1995 | Baeten et al. | 607/28 |
| 5,476,509 | 12/1995 | Keogh et al. | 623/1 |
| 5,536,258 | 7/1996 | Folden | 604/265 |
| 5,556,708 | 9/1996 | Horl et al. | 427/385.5 |
| 5,607,475 | 3/1997 | Cahalan et al. | 427/2.24 |
| 5,670,097 | 9/1997 | Duan et al. | 264/1.24 |
| 5,672,638 | 9/1997 | Verhoeven et al. | 427/2.25 |

OTHER PUBLICATIONS

VonRecum A.f., Barth E., Implant Infection, *J. Invest. Surg.*, 2:351, 1989. (no month).

Stamm, W.E., Infections Related To Medical Devices, *Ann.Intern.Med.* 89:764, 1978 (Nov.).

Dankert J., et al, Biomedical polymers; Bacterial Adhesion, Colonization and Infection, *CRC Crit.Rev.Biocompat.* 2:219, 1986 (no month).

Norden C.W., A Critical Review of Antimicrobial Prophylaxis in Orthopedic Surgery, *Rev.Infect.Dis.* 5:928,1983 (Sep.).

Golomb, G., Shpigelman A., Preventionof Bacterial Colonization on Polyurethane in vitro by Incorporated Antibacterial Agent, *J. Biomed.Mater.Res.*, 25:937, 1991 (Aug.).

Bayston R., Milner R.D.G., Antimicrobial Activity of Silicone Rubber Used in Hydrocephalus Shunts, After Impregnation With Antimicrobial Substances, *J.Clin.Pathol*, 34:1057, 1981. (no month).

(List continued on next page.)

*Primary Examiner*—Diana Dudash
*Attorney, Agent, or Firm*—Daniel W. Latham; Harold R. Patton

[57] ABSTRACT

To minimize the incidence and consequences of device related infection that occur after prosthetics implants of neuro-muscular stimulating devices, an infection resistant intra-muscular lead has been developed and is disclosed herein. Infection incidence has been decreased by using biomaterials able to release antibacterial drugs (gentamicin) at a controlled rate for the first 3–6 weeks after implant.

26 Claims, 9 Drawing Sheets

OTHER PUBLICATIONS

Jansen, B. et al, Antibiotic–Containing Polyurethanes For the Prevention of Foreign–Body Infections; in *Progress in Biomedical Polmers,* Gebelein C.G.,Dunn R.L., eds. Plenum Press,New York, pp.347–354,1990.(no month).

Olanoff L.S., et al, Sustained Release of Gentamicin From Prosthetic Heart Valves, *Trans. ASAIO,* 25:334,1979.(no month).

Remington's Pharmaceutical Sciences, 8th ed., Mack Publishing Co., Easton, Pennsylvania, USA p. 1203,1990(no month).

Dougherty S.H. Simmons R.L., Infections in Bionic Man: The Pathobiology of Infections in Prosthetic Devices–Part 1, *Curr.Probl.Surg.* 19:217,1982, (May).

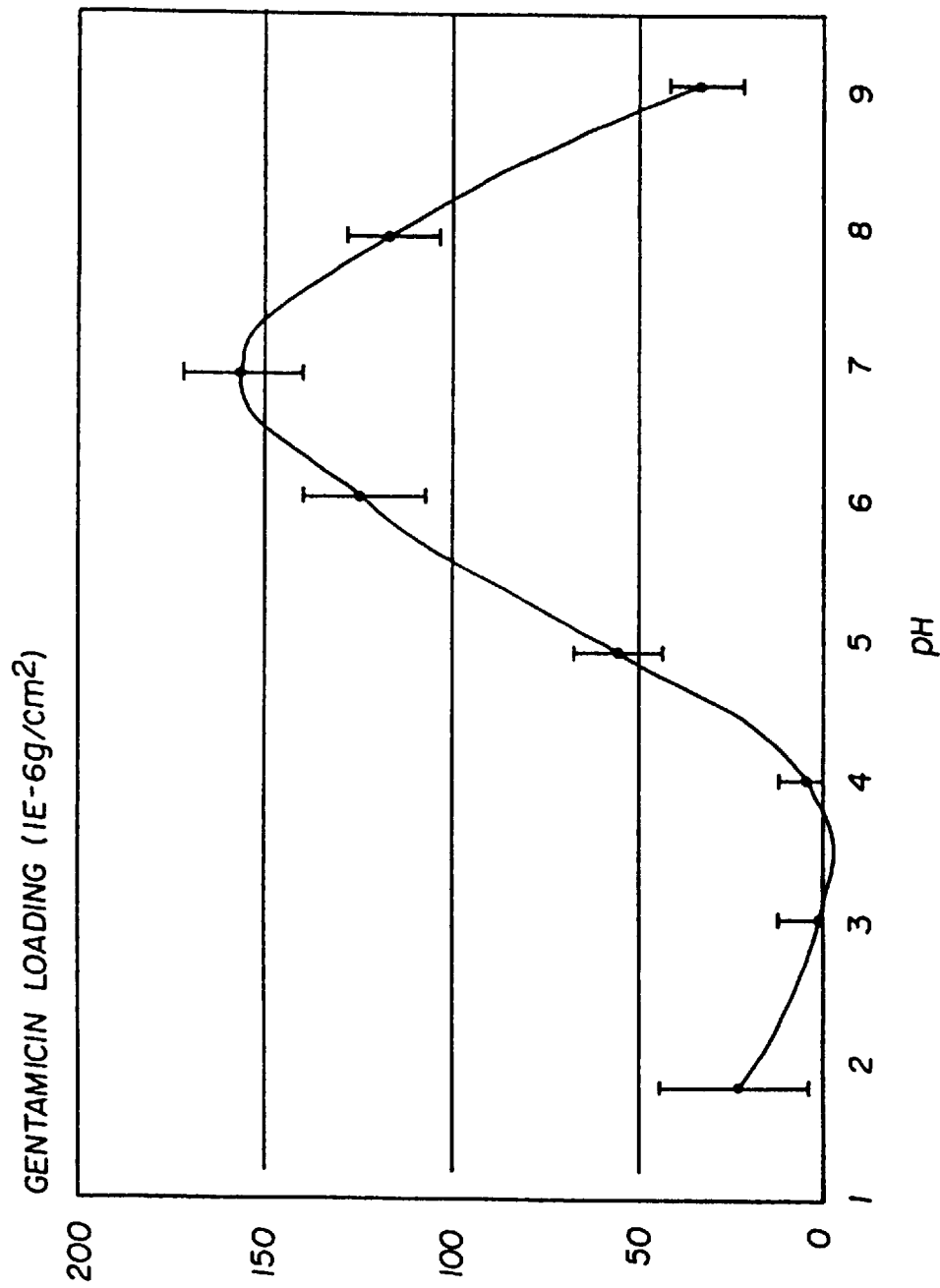

INTRAMUSCULAR STIMULATION LEAD WITH ENHANCED INFECTION RESISTANCE

This is a divisional of copending application Ser. No. 08/553,206 filed on Nov. 7, 1995.

BACKGROUND OF THE INVENTION

This invention relates generally to method and apparatus for electrical muscle stimulation for various applications and particularly to method and apparatus for improving the function of a long-term muscle stimulating implant lead with respect to enhanced infection resistance thereof. This invention relates more specifically to surface treatment and mechanical design of an implantable lead that provides controlled anti-microbial release.

The use of implants and medical devices has become widely accepted in the various clinical fields, and has shown a tremendous growth during the past three decades. Clinical use of these mostly synthetic devices is not completely free of complications. Current clinical experience teaches us that implant infection is most often irreversible and necessitates implant removal. The incidence of device-related infections is approximately 1 to 10% in patients with implanted prosthetic devices and is one of the most frequently clinically important complications of implanted materials.

Approaches to reduce device-related infections initially were focused on improvements of the surgical technique, including modification of the operating room area and the use of prophylactic antibiotics at the time of surgery.

Although the incidence of infections has reduced, device-associated infections still occur in a significant fashion. Currently efforts are increasingly directed on the role of the implant itself, and consequently on modification of the material to enhance the infection-resistance of the device.

Most reported technologies involve the release of antimicrobial compounds from the material to enhance the infection-resistance. The ability of a sustained antimicrobial releasing device to selectively deliver optimal amounts of the agent to the surrounding tissues offers an alternative to conventional prophylactic antimicrobial therapy in minimizing postoperative complications of infection.

While most strategies involved the impregnation of the substrate material with antimicrobial agent, a technique is described herein involving controlled release of antimicrobial agent from a surface graft matrix. Such an approach will prevent deterioration of the substrate material to a level precluding practical application.

A similar technique is disclosed in U.S. Pat. No. 5,344,455, assigned to Medtronic, Inc. (also assignee of the present invention); however, contrary to the presently disclosed technique no control on antimicrobial loading and release was shown. It is demonstrated herein that control of the surface graft matrix composition can be advantageous regarding loading and release of the antimicrobial agent, and consequently regarding bactericidal activity and elicited cytotoxicity. Therefore, the disclosed technique is an improvement over that of U.S. Pat. No. 5,344,455.

The concept presently disclosed involves a copolymer surface graft with a controlled copolymer composition. The copolymer surface graft is preferably designed to release one hundred percent of the drug in a 3 to 6 weeks time span.

Although the invention is generally applicable to improved surface treatment of implantable articles of all kinds, it will be described herein with specific reference to implantable leads and more particularly with reference to muscle stimulation leads.

While much of the prior art neuro-muscular stimulation techniques have been applied to functional restoration of movements, other types of skeletal muscles have also been involved, even including those transplanted from one area of the body to another to improve the performance of an organ. One form of muscle stimulation apparatus is disclosed in U.S. Pat. No. 4,735,205, issued Apr. 18, 1988 to Juan C. Chachques et al. and assigned to Medtronic, Inc. The above-identified patent includes identification of a large group of related U.S. patent documents and other publications which provide a thorough identification of the background of the muscle stimulation art. These references are incorporated by reference in the present application to provide suitable orientation information for practicing the present invention.

Enhanced infection resistance is particularly important when electrical muscle stimulation apparatus is used in an anal dynamic myoplasty procedure. This is the subject matter to which this invention is most specifically directed. In the past, the infection rate in such procedures has been around 20 percent with half of them being located near or within the intramuscular lead apparatus. This invention concerns an improved intramuscular lead with specific surface treatments which have been shown to be efficacious in implant studies to prevent device related infectious complications.

SUMMARY OF THE INVENTION

This invention relates in its most preferred embodiment to method and apparatus for electrical muscle stimulation at numerous different muscle implant locations but most particularly for use with a gracilis or gluteus muscle implant to correct fecal incontinence or urinary incontinence and most particularly for use with a rectal muscle implant in anal myoplasty procedures. The invention is however of general applicability to implantable articles.

In the context of the present invention such apparatus is implanted in a selected muscle to produce stimulation of that muscle. A pulse generator, located outside of the sterile field, produces a measured electrical current to an electrode whereby a threshold measurement can be performed from outside the sterile field in order to determine the maximum muscle reaction to the current supplied through the electrode to the selected muscular area. This produces comparative threshold measurements to determine the optimum location for a permanent implant electrode. A variety of arrangements have been used for determining the best implant location of a stimulating muscle electrode and are more fully described in U.S. Pat. No. 5,425,751, which is incorporated herein by reference.

Once an implant site is selected an operational stimulating implant electrode is inserted into the muscular tissue to be stimulated at the determined optimum location.

The design of the lead preserves the possibility of adjusting the exposed electrode length as described in U.S. Pat. No. 4,735,205 while minimizing the dead space volume where infection could develop. The content of U.S. Pat. No. 4,735,205 is fully incorporated herein by reference.

The surface treatment of the invention involves the surface grafting of the monomers acrylic acid and acrylamide in a controlled ratio. Control of the copolymer composition is required for controlled loading and release of positively charged drugs, such as the antimicrobial agent gentamicin; the latter being the preferred drug for the described device-application. Controlled loading and release has been shown of major importance in in vitro and in vivo tests with regard to cytotoxicity and antibacterial activity. The copolymer surface graft is preferably designed to release one hundred percent of the drug, in a 3 to 6 weeks time span post-implantation. Gentamicin loading is achieved by ionic interaction of the negatively charged copolymer graft with the positively charged drug. The gentamicin release profile is mainly determined by the physical configuration of the surface graft matrix. Ion-exchange is the mechanism by which the gentamicin will be released.

As already indicated herein, a primary purpose of the present invention is to enhance the infection resistance of implantable articles including operational stimulating implant electrode apparatus by providing specific surface treatments which enhance resistance to infection.

BRIEF DESCRIPTION OF THE FIGURES

FIG. 4 is a graph showing gentamicin loading as a function of pH.

DETAILED DESCRIPTION OF THE INVENTION

In U.S. Pat. No. 4,735,205 a typical intramuscular lead apparatus sometimes referred to as an electrical muscle stimulation apparatus is disclosed in columns 7 and 8 for electrical stimulation of a muscle. FIG. 4 of said patent has been substantially reproduced at least in part as FIG. 1 of the present application which, along with the other Figures, provides the necessary background information and an illustrative apparatus to disclose the improvement of the present invention.

Figure 1:
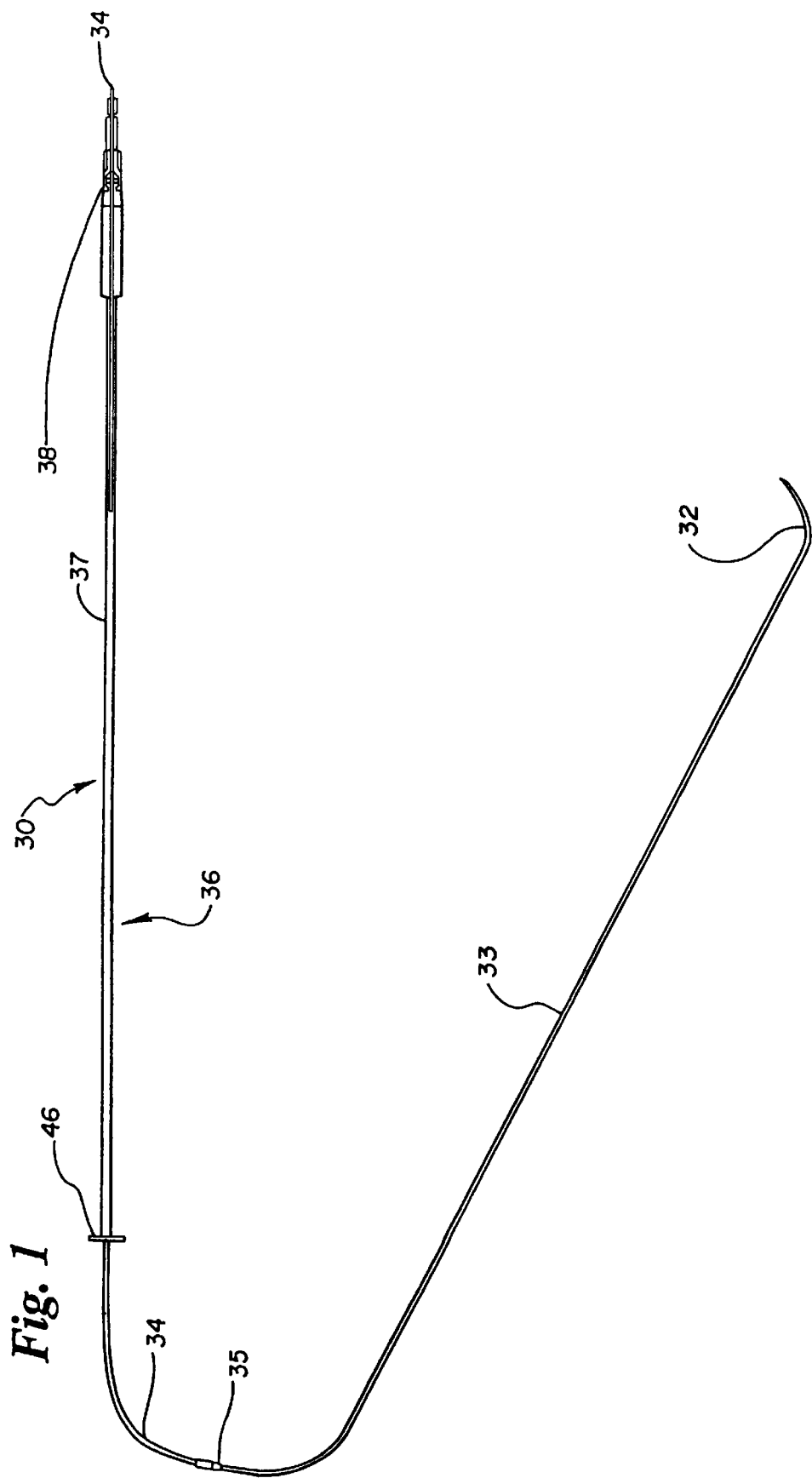
FIG. 1 is a schematic diagram of one embodiment of an intramuscular lead which may make use of the present invention.
Figure 2:
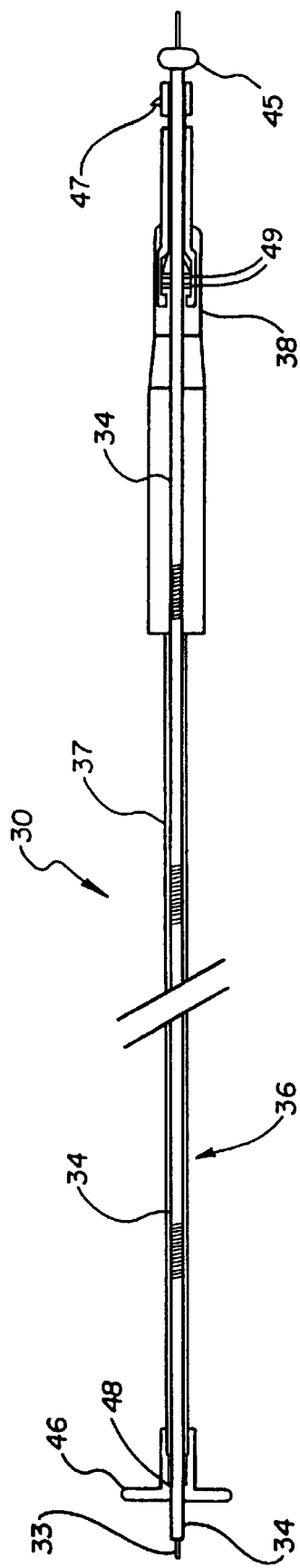
FIG. 2 is a schematic cross-sectional view of the lead of FIG. 1 with the fixation disk and the locking mechanism of the electrode coil, located in the connector section.

Referring now to FIGS. 1 and 2, they show an apparatus which is adapted to be coupled to a pulse generator, the apparatus comprising an intramuscular lead generally designated at 30 which includes a suture needle 32 (shown in FIG. 1 only), adapted to be drawn through the muscle to be implanted, a non-conductive line 33, an electrode 34, an electrode tip 35, a lead body 36 and a connector 38. Electrode 35 is implanted in a muscle by being drawn into the muscle by the non-conductive line 33 which is attached to the suture needle 32, which needle is inserted through the muscle by the surgeon in a manner well-known in the art. The connector 38 is adapted to be coupled to one of the output terminals of the pulse generator after electrode 35 has been implanted in the muscle tissue (not shown) at an appropriate location.

The electrode 34 shown in FIGS. 1 and 2 comprises a length of coiled wire conductor 34 (best seen in FIG. 2) extending between distal end of electrode tip 35 and connector 38. The coiled wire conductor of electrode body 34 may consist of platinum-iridium or other electrode materials. The lead conductor is insulated by an insulating tube or covering 37 which extends from anchoring disk 46 back to the connector 38.

Before implanting the electrode into the muscle, the electrode surface is fully exposed by sliding the electrode coil 34 out of the lead body by pulling on the line 33 and holding the fixation disk 46. The electrode is fully exposed when the limiter 45 hits the connector pin 47 (FIG. 2). The coil 34 is first unlocked by turning connector pin 47 (FIG. 2) counter-clockwise. After placing the electrode tip 35 in the muscle, needle 32 and length of line 33 are severed at the distal end of the coil 34. A length of line 33 may alternately be employed to fix the electrode by tying or clipping it to the muscle. The electrode length is adjusted by holding the electrode coil at the end of the connector 38, and by pushing the connector 38 until the fixation disk 46 is in contact with the muscle epimysium. The coil 34 is locked again by turning the connector tip 47 clockwise. The lead is delivered with the most usually exposed electrode length used (25 mm for dynamic graciloplasty), therefore no electrode adjustment may be required in most implants. The disk 46 can then be sutured to the muscle using sutures or staples. Disk 46 has sealing rings 48 (FIG. 2) preventing free fluid movements between the inner lead body cavity and body fluids; this minimizes the amount of blood that penetrates the lead body by capillarity during the implant procedure, and therefore possible contamination of the lead. Also, the antibiotic released by the coating in the lumen of the lead body will reach a high bactericidal concentration preventing any bacteria to develop inside the lumen of the lead.

Figure 3A:
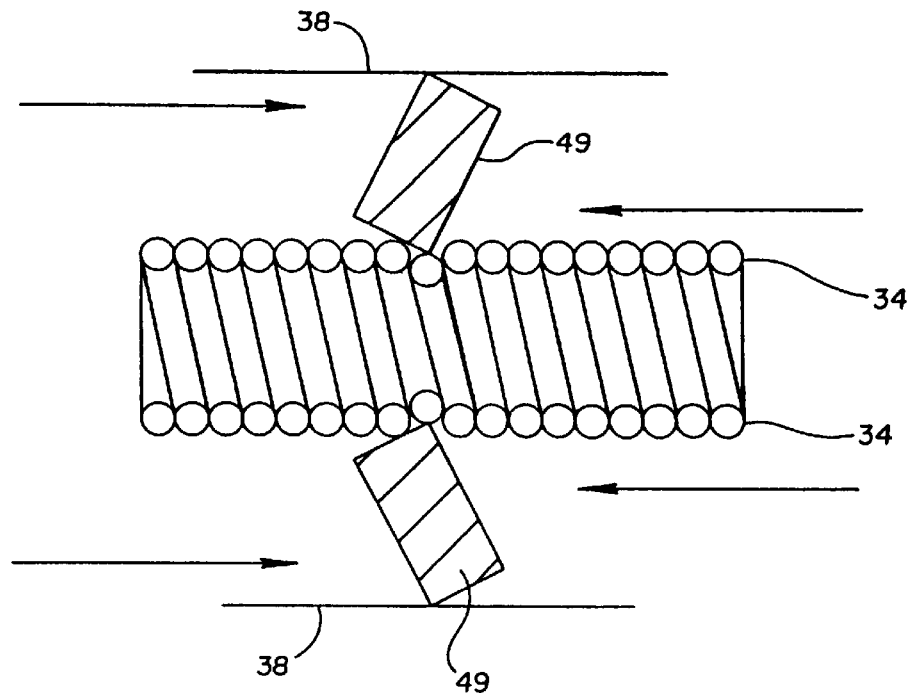
FIG. 3a and 3b schematically shows the principle of a locking mechanism using metal rings (FIG. 3a locked/FIG. 3b unlocked).
Figure 3B:
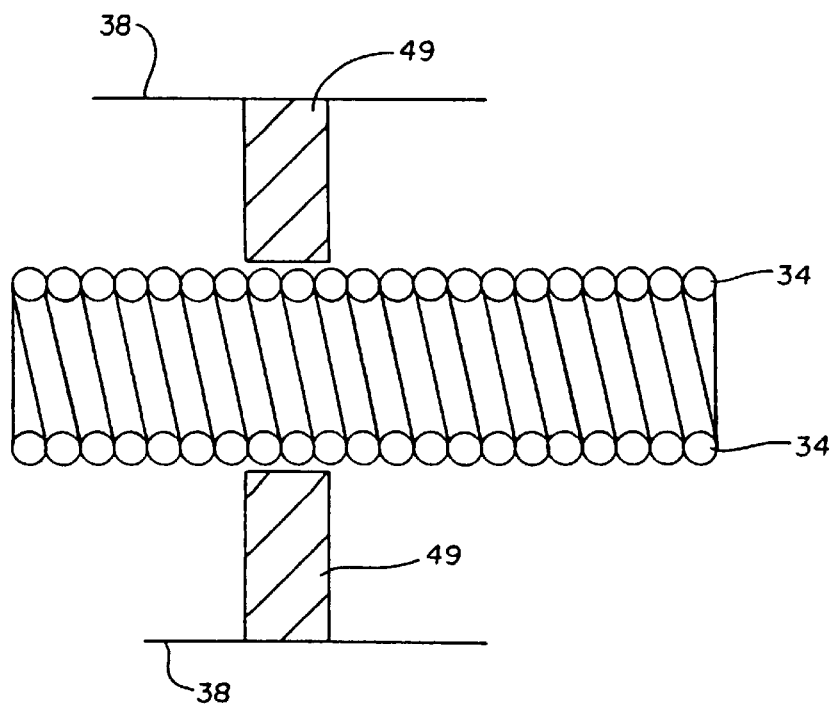

There are various arrangements which may be used to fixate the position of electrode coil 34 in the lead connector, such as:

using a set-screw connection (not shown) to tighten the electrode coil to the lead connector. Due to this connection technique the lead connector tends to be large and bulky which is a disadvantage.

using a metal ring (disk) connection shown in FIGS. 3a and 3b. Within the lead connector several fixation disks 49 are placed. Inside these disks, the electrode coil 44 can move freely in longitudinal direction. By turning the disks with application of lateral forces as indicated by the arrows, over several degrees the coil will be locked (FIG. 3a). The unlocked position is shown in FIG. 3b. The electrode coil can be fixed to the lead connector by rotating in opposite direction the connector-pin 47 versus the lead connector, the pin will move in longitudinal direction along a screw-thread mechanism and tightens the coil. This motion will force the disks to rotate resulting in a mechanical and electrical lock. Once the electrode coil length is adjusted, the remaining electrode section can be removed by using a pair of scissors. The complete design is small enough so it can be placed in the interior of the lead connector.

As can be seen from the above description of the apparatus, it is comprised of various elements of a generally coaxial interrelated structure wherein the elements have inner and outer surfaces which are surface treated in accordance with this invention to enhance infection resistance. For example, the lead body and the fixation disk are coated on their inner and outer surfaces in accordance with the invention. Other parts of the leads like the non-conductive line 33 or the insulated parts of the connector 38 may be treated as well.

The surface treatment involves covalently grafted acrylic acid and copolymers thereof. More specifically, it involves the use of controlled copolymer ratios required for controlled loading and release of drugs. A preferred drug for the instant electrode application is an antibiotic positively charged such as gentamicin. In vivo and in vitro experiments have shown the importance of controlling loading and release with regard to cytotoxicity. One hundred percent of the drug is released, preferably in the four week period following the implant of the lead or other implantable device. The coating is preferably applied on both inner and outer surfaces of the lead body sliding sheath and fixation disk.

The surface treatment or coating as described more fully hereinbelow provides a method for controllably loading an antimicrobial into a graft matrix, and not just by ionic attachment, and for likewise controllably releasing the drug.

Other polymeric substrates may be used herein and all such are generally referred herein to as polymeric substrate (s) or articles having a polymeric surface. Such materials are otherwise biologically inert polymeric material.

Surface Treatment or Coating

The invention is aimed at providing implantable articles, and specifically an apparatus for electrical muscle stimulation, with a surface treatment that enhances the infection resistance thereof The developed technology involves the covalent surface grafting of a water soluble polymer onto a substrate material. Surface grafting is preferably initiated by the ceric ion method, previously disclosed in U.S. Pat. No. 5,229,172, assigned to Medtronic, Inc. While ceric ion initiation is the most preferred method to graft monomers to substrate surfaces, it is obvious that other grafting techniques may be used as well. Known examples of other initiation methods include corona discharge, UV irradiation and ionizing radiation.

While polyetherurethane is the preferred polymeric substrate in the context of this invention, the substrate material can be any polymeric surface, such as polyurethane or any of the well known inert biocompatible polymer materials, including polyamides, polycarbonates, polyethers, polyesters, polyolefins, polystyrene, polyurethane, polyvinyl chlorides, silicones, polyethylenes, polypropylenes, polyisoprenes, and polytetrafluoroethylenes.

Additionally, the substrate material can be a metallic surface, such as titanium or tantalum or any of the well known inert biocompatible metallic materials, including stainless steels such as MP35N and 316L such as is found in IPG cans, intravascular stents and the like.

A copolymer graft of acrylic acid (AA) and acrylamide (AAm) having the antimicrobial drug gentamicin ionically coupled is the preferred embodiment in the context of this invention. The copolymer graft of acrylic acid and acrylamide has a controlled composition to assure controlled loading and release of the antimicrobial drug gentamicin. The copolymer graft is preferably designed such that one hundred percent of the drug gentamicin is released in a 3–6 weeks time span post-implantation.

While acrylic acid and acrylamide are the preferred monomers from which the copolymer surface graft is composed, the surface graft polymer can be composed from other vinyl-functional monomers, such as N-(3-aminopropyl) methacrylamide (APMA) 2-hydroxyethyl methacrylate (HEMA), 2-acrylamido-2-methylpropane sulfonic acid (AMPS) and copolymers thereof, for example.

The acquired hydrophilic graft polymer consequently forms the matrix in which a charged antimicrobial drug can be ionically bonded. The graft polymer contains pendant groups having an ionic charge and the antimicrobial agent has an ionically opposite charge to the graft polymer pendant groups. Ionic coupling of antimicrobial agents is achieved by simple immersion of the surface-grafted material in a solution of controlled pH of the desired antimicrobial agent.

The surface graft polymer will be permanently covalently bonded by graft polymerization to the substrate. These graft polymers lend themselves to ionic coupling, when selected to provide an appropriate charge dissimilar to that of the antimicrobial agent, with various antimicrobial agents, which are selected due to their ionic nature. Ionic coupling of the antimicrobial agent to the graft polymer may be achieved by simply immersing the surface-grafted polymer in a solution of controlled pH of the desired antimicrobial agent.

Specifically, a number of graft coatings may be used in accordance with this invention. The most preferred are comprised of monomers grafted onto the substrate surface via ceric ion initiation. Monomers containing cationic as well as anionic pendant groups may be grafted. An example of the former is N-(3-aminopropyl) methacrylate (APMA) and copolymers thereof, while a prime example of the latter is acrylic acid (AA) and copolymers thereof. To those familiar with this art it will be obvious that, via chemical modification techniques, cationic surface grafts can be chemically converted to anionic surface grafts and anionic surface grafts can be chemically converted to cationic surface grafts. These charged surface graft matrices lend themselves to the ionic coupling of charged antimicrobial agents. Control of the surface graft polymer composition allows control on loading and release of the antimicrobial agent.

Examples of cationic antimicrobials that can be loaded to negatively charged surfaces are shown in the table below. It is obvious that the table below is not complete and various other cationic antimicrobials may have been included.

TABLE 1

| List of cationic antimicrobial agents | |
| --- | --- |
| gentamicin | amikacin |
| streptomycin | paromonycin |
| neomycin | tobramycin |
| kanamycin | silver ion |

Examples of anionic antimicrobials that can be loaded to positively charged surfaces are shown in the table below. It is obvious that the table below is not complete and various other anionic antimicrobials may have been included.

TABLE 2

| List of anionic antimicrobial agents | |
| --- | --- |
| ampicillin | norfloxacin |
| cefazolin | sulfadiazine |
| oxacillin | cephalothin |
| cephalosporin | |

Additionally, the graft polymers may lend themselves to covalent coupling of antimicrobial agents, when capable to provide a functional chemical group appropriate for the covalent coupling of antimicrobial agents. Covalent coupling of antimicrobial agents must not mediate the bactericidal activity of the antimicrobial agents or interfere with the to mechanism of action of the antimicrobial agents. Since most antimicrobial agents demonstrate bactericidal activity when ingested by the bacterial cell, it may be that covalent coupling will largely decrease, if not completely inhibit the effectiveness of the antimicrobial agent. However, one can distinguish a group of antimicrobial agents that kill bacteria by virtue of their effect on the permeability of the cell membrane. Covalent coupling of these antimicrobial agents may be suitable for the development of articles with enhanced infection resistance. Examples of the latter group of antimicrobial agents are Polymyxin B, Colistin, Gramicidin A.

1: Ceric ion initiated surface graft copolymerization

Extruded Pellethane 55D films were ultrasonically cleaned in IPA for 15 minutes prior to ceric ion initiated surface grafting. FT-IR investigation has demonstrated that 15 minutes IPA-treatment is sufficient to remove any surface contamination that originates from processing aides, such as bis-stearamide waxes, that may interfere with the grafting process. Immediately after the IPA-cleaning, samples were dried in a forced air oven at 50°–60° C. for approximately 5 minutes. Meanwhile, an aqueous grafting solution was prepared that was composed of 40% bw total monomer concentration, containing acrylic acid monomer and acrylamide monomer in varying monomer ratios, 6 mM of ceric ammonium nitrate (CAN) and 0.06M nitric acid ($HNO_3$). Prior to grafting, the grafting solution was treated to remove excess air by exposure to reduced pressure (18 mmHg±5 mmHg) for a maximum of 2 minutes.

Grafted samples (10×1 cm strips) were prepared by placing the cleaned and dried samples in an appropriate volume of the grafting solution. Grafting was allowed to continue for 15–20 minutes at 30° C., while stirring the solution.

Following grafting, the samples were rinsed in DI water to stop the grafting process as well as to clean the surface graft matrix formed. Thorough clean-up of the grafted samples was performed in a phosphate buffered saline (PBS) solution, pH=7.4, for 16–18 hours at 50°–60° C. ESCA data revealed that the surface graft copolymer composition agreed very well with the monomer ratio employed.

2: Gentamicin loading of anionic surface grafts prepared from acrylic acid and acrylamide monomer 55D Pellethane samples were surface grafted as previously discussed. Subsequently, the surface grafted samples were immersed in a 0.01M MES buffered aqueous solution, pH=6.0, for a minimum of 30 minutes. The surface grafted samples were then immersed in a 0.01M MES buffered aqueous solution of gentamicin sulfate, pH=6.0. The buffered gentamicin sulfate solutions typically contained 0.5 mg/ml gentamicin base. The sample immersion typically lasted 30 minutes; a volume to surface ratio of 2:1 (ml:cm$^2$) was typically used for the gentamicin loading process. Upon completion of the immersion, the samples were removed, rinsed for 5–10 seconds in DI water, allowed to air dry, and stored.

3: Quantitative analysis of gentamicin in aqueous solutions

Gentamicin containing aqueous solutions, standards as well as samples, were analyzed by means of a TNBS assay. Gentamicin containing solutions were adjusted to pH=9 by addition of 0.1M borate, after which 25 µl 0.03M aqueous TNBS was added per ml of sample solution. The TNBS derivatization reaction was allowed to proceed for 25–30 minutes at room temperature, after which the UV absorbance at 415 nm was measured, while 595 nm was used as the reference wavelength.

4: Quantitative analysis of gentamicin in anionic surface grafts prepared from acrylic acid and acrylamide monomer 55D Pellethane samples were surface grafted and gentamicin loaded as previously disclosed. Subsequently, the gentamicin solutions used for loading the surface grafted samples were analyzed for their gentamicin contents by the TNBS assay. The difference in gentamicin content before and after sample immersion was determined and used as measure for the amount of gentamicin loaded. The amount of gentamicin loaded was typically expressed as $\mu g/cm^2$.

5: Effect of pH on gentamicin loading of anionic surface grafts prepared from acrylic acid monomer 55D Pellethane samples were surface grafted with acrylic acid monomer as previously discussed. Gentamicin stock solutions were prepared that were buffered at different pH values. Typically the solutions contained 0.01M of the desired buffer agent. The pH-range extended from pH=2 to pH=9. After immersion of the surface grafted samples in the corresponding buffered solutions without gentamicin, surface grafted samples were gentamicin loaded, and the amount of gentamicin loaded was determined as previously described.

It was determined that the gentamicin loading could be controlled by the pH, as is displayed in FIG. 4. The optimal pH-range for gentamicin loading extends from pH=6 to pH=8.

6: Effect of time on gentamicin loading of anionic surface grafts prepared from acrylic acid monomer 55D Pellethane samples were surface grafted with acrylic acid monomer as previously discussed. Gentamicin loading was performed as previously discussed, except for the exercised variation in immersion-time. Gentamicin loading of the anionic surface graft matrix was determined as discussed above.

Gentamicin loading showed a linear profile during the first 15 minutes, with a velocity that approximately was equal to 9.5 $\mu g.cm^{-2}.min^{-1}$. Thereafter, the velocity of gentamicin loading reduced and the loading profile became asymptotic. Between 20 minutes and 30 minutes additional gentamicin loading was negligible.

7: Effect of crosslinking-density of surface graft matrix on gentamicin release from anionic surface grafts prepared from acrylic acid monomer 55D Pellethane samples were surface grafted with acrylic acid monomer as previously described, except for the addition of methylene-bis-acrylamide as crosslinking reagent during surface graft copolymerization. Surface grafted samples were gentamicin loaded, and the amount of gentamicin loaded was determined as discussed above.

Gentamicin release was performed by immersion of gentamicin loaded samples in phosphate buffered saline (PBS) at 37° C.; a volume to surface ratio of 1:1 (ml:cm$^2$) typically was used throughout the experiment. At desired time points the samples were withdrawn from the solution and immersed in fresh PBS. Solution samples were analyzed for their gentamicin content by means of the TNBS assay.

It was demonstrated that with increasing crosslinking density the gentamicin release is slower. This is obviously in agreement with what one would expect. However, since the non-crosslinked graft did not completely release one hundred percent of its gentamicin in the desired 6 weeks time span, another design of the surface graft matrix had to be developed to obtain the desired gentamicin release profile, i.e., one hundred percent gentamicin release within a 3 to 6 weeks time span.

8: Effect of charge-density of surface graft matrix on gentamicin loading of anionic surface grafts prepared from acrylic acid and acrylamide monomer Ceric ion initiated surface grafting was performed as previously described. The charge-density of the surface graft matrix was varied by variation of the monomer ratio of the monomers acrylic acid and acrylamide. While acrylic acid contains an anionic pendant group, acrylamide contains a neutral pendant group. Variation of the monomer ratio, thus will allow preparation of surface grafts with varying charge-density. Subsequently, surface grafted samples were gentamicin loaded, and the amount of gentamicin loaded was determined as previously described.

Figure 5:
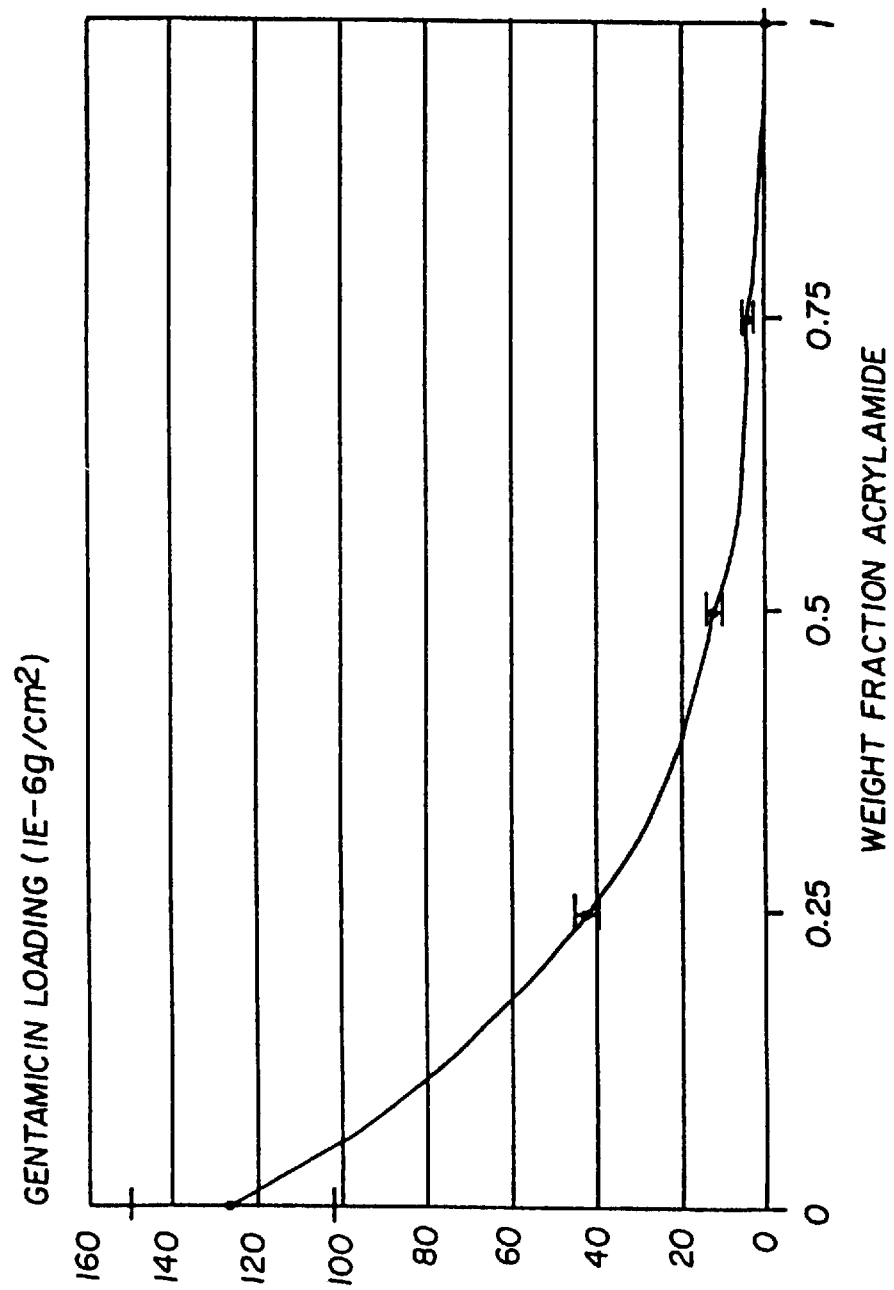
FIG. 5 is a graph showing gentamicin loading as a function of copolymer composition.

The results are displayed in FIG. 5; with an increasing acrylamide fraction of the surface graft matrix the gentamicin loading diminishes. These results are obvious and once more demonstrate that the ionic interaction between the cationic antimicrobial agent gentamicin and the anionic surface graft matrix is the driving force for drug immobilization.

9: Effect of charge-density of surface graft matrix on gentamicin release from anionic surface grafts prepared from acrylic acid and acrylamide monomer Surface grafted 55D Pellethane samples ranging in charge density were prepared and gentamicin loaded as previously described. Gentamicin release was performed by immersion of gentamicin loaded samples in phosphate buffered saline (PBS) at 37° C.; a volume to surface ratio of 1:1 (ml:cm$^2$) typically was used throughout the experiment. At desired time points the samples were withdrawn from the solution and immersed in fresh PBS. Solution samples were analyzed for their gentamicin content by means of the TNBS assay.

Figure 6:
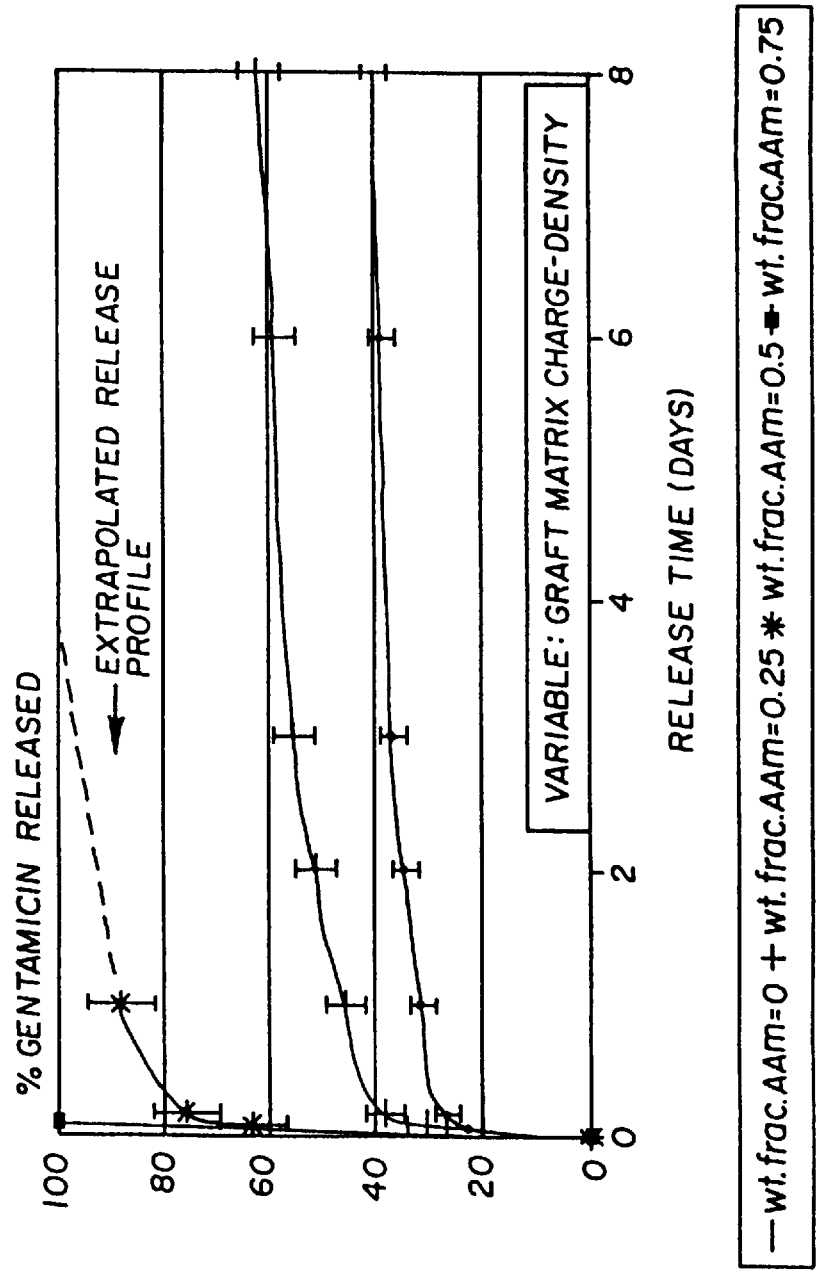
FIG. 6 is a graph showing gentamicin release from anionic surface graft matrix.

From FIG. 6 it can be concluded that variation of the monomer ratio of the monomers acrylic acid and acrylamide is the preferred "tool" for manipulation of the gentamicin release profile, such that the desired release profile is achieved. The preferred surface graft matrix would be composed of an acrylic acid/acrylamide copolymer containing an acrylic acid fraction of 50–75%. Most preferably, the acrylic acid fraction would be in the range of 65–75%.

Figure 7:
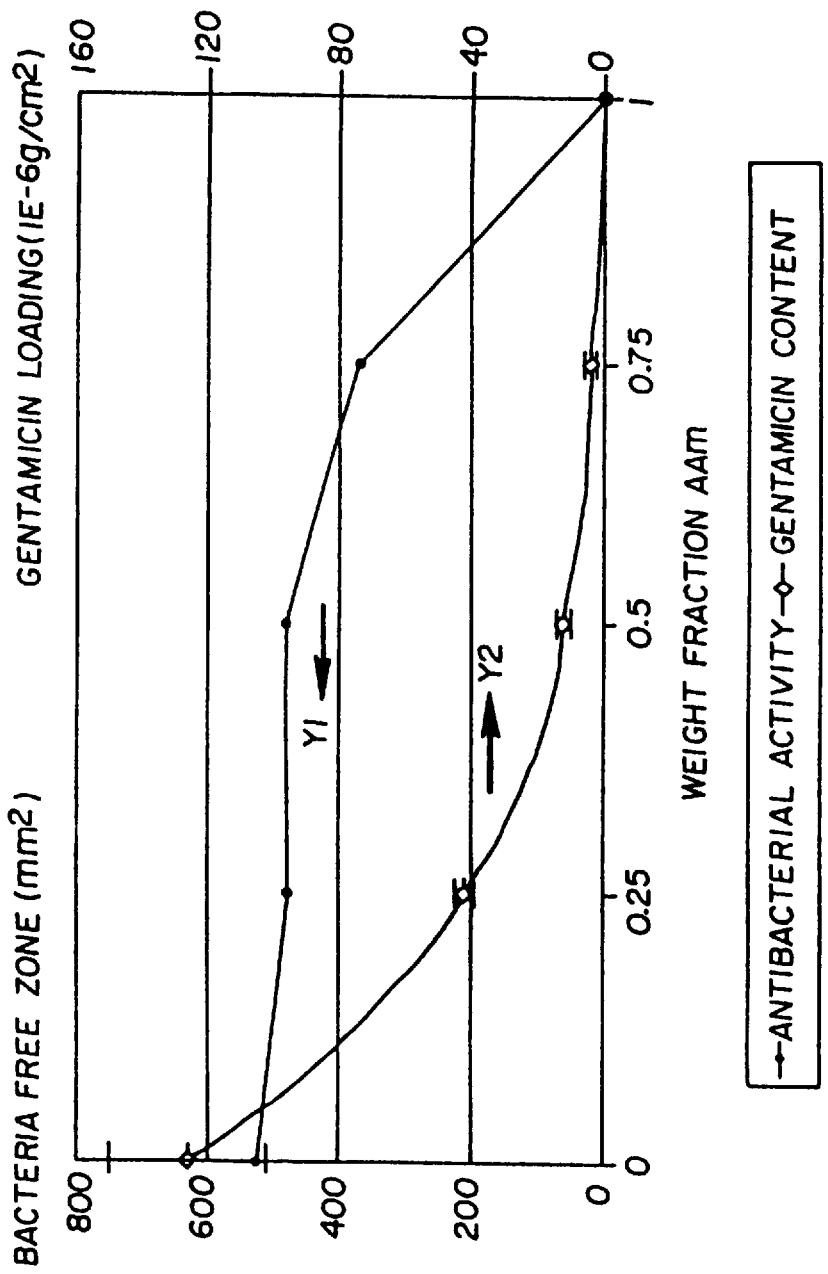
FIG. 7 is a graph showing in vitro bactericidal activity as a function of copolymer composition.

10: Evaluation of in vitro antibacterial activity of gentamicin loaded samples with varying charge-density Surface grafted 55D Pellethane samples ranging in charge density were prepared and gentamicin loaded as previously described. The antibacterial activity was determined by a "zone-of-inhibition" test. A Isosensitest agar plate was seeded with bacteria, for which typically a suspension of $\pm 10^4$ *Staph. aureus*/ml saline was used. Subsequently, the test materials were applied (8 mm discs); typically Genta-neo-sensitab (Rosco Diagnostica, Taastrup, Denmark), a gentamicin-loaded tablet was used as the positive control. Surface grafted samples without gentamicin were applied as negative controls. Subsequently, the agar plate is incubated overnight at 37° C. The following day the plate was removed from the incubator and the bacteria free zone around each sample is determined. The regions of bacterial growth and inhibition are obvious visually. The results of this experiment are displayed in FIG. 7. It can be concluded that reduced gentamicin loading, as a consequence of increased acrylamide fraction, was compensated for by a faster release and as such was not of major influence on the bactericidal activity.

11: Evaluation of in vitro cytotoxicity of gentamicin loaded samples with varying charge-density It is known that gentamicin may elicit toxicity when applied in too large amounts. It is therefore of key importance to evaluate whether or not the developed surface grafted samples do demonstrate cytotoxic features due to the gentamicin release.

Surface grafted 55D Pellethane samples ranging in charge density were prepared and gentamicin loaded as previously described. The cytotoxicity was determined according to the method of Van Luyn et al. In short, this method involves a 7 day exposure of the test material to a methylcellulose culture of human fibroblasts; this test method has been reported to be more sensitive than the established test methods.

Figure 8:
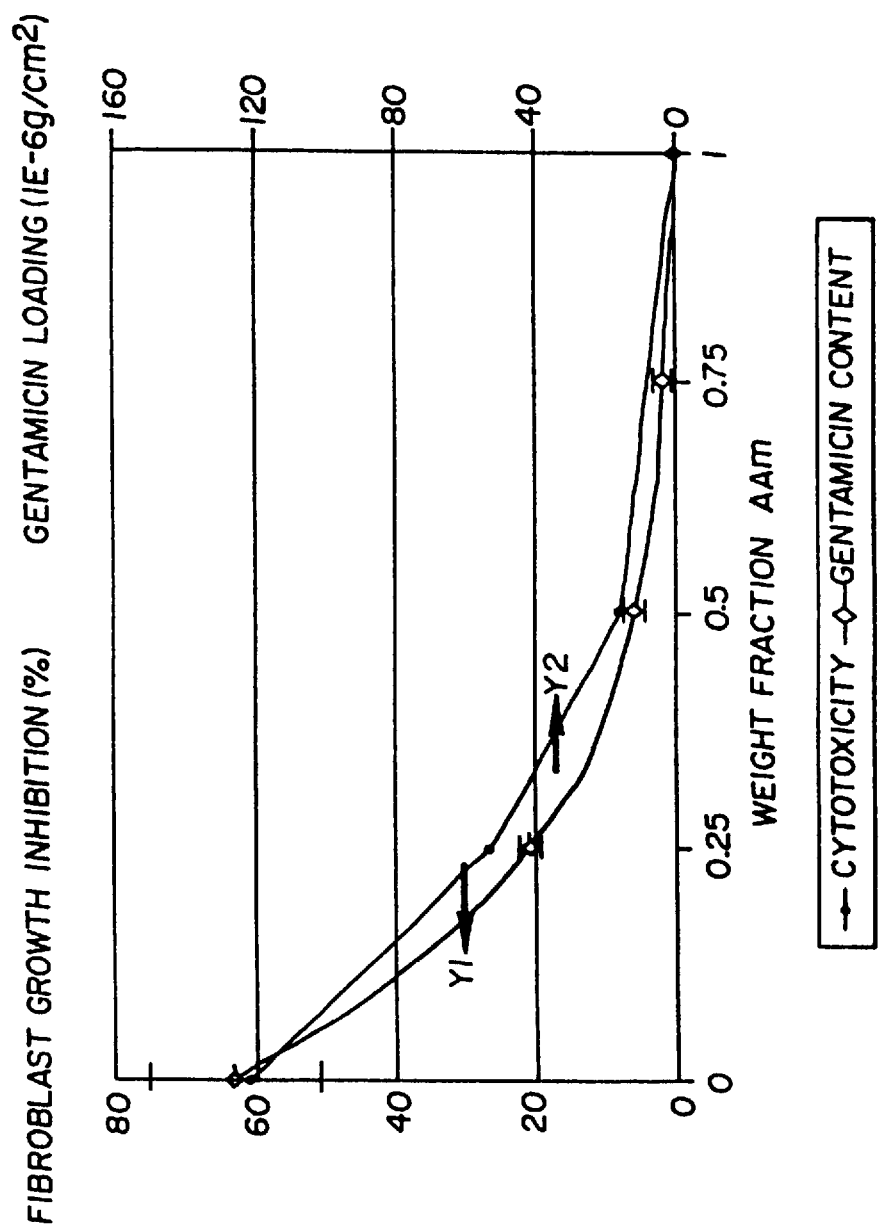
FIG. 8 is a graph showing in vitro cytotoxicity as a function of copolymer composition.

The results are displayed in FIG. 8. This test confirms the toxicity of gentamicin. A dose-related response was identified, which emphasizes the need for a designed surface graft matrix, that controls the release rate of gentamicin and consequently prevents manifestation of cytotoxic events.

The results disclosed in EXAMPLES 9 to 11 emphasize the importance of control of the copolymer composition of the surface graft matrix. The preferred copolymer graft composition is designed such that it has an appropriate balance between release rate, bactericidal activity, and biocompatibility (non-cytotoxicity).

12: Evaluation of in vivo performance—a comparative animal implant study
summary description of implant study Polyurethane lead samples with a length of ±5 cm (see FIG. 9) were used as a representative model for clinically used implantable leads, and as such identical materials were used in the manufacturing.

Figure 9:
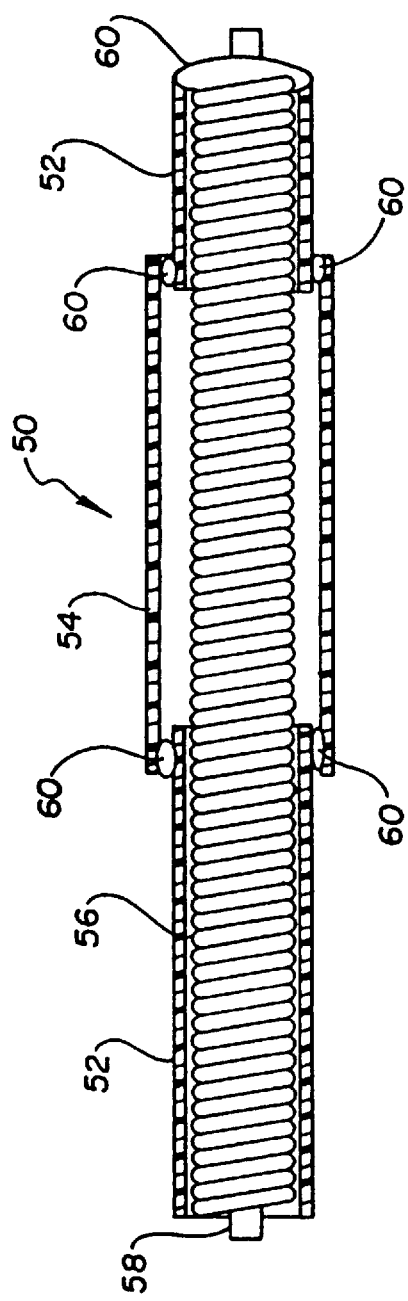
FIG. 9 is a representative schematic model of clinically used leads.

FIG. 9 shows such a clinically used lead generally designated 50. The lead includes tapered polyurethane tubing 52 and 54, a platinum-iridium coil 56, a polypropylene blue wire 58 and polyurethane adhesive 60. Dimensions of the lead are also shown in the Figure.

Surface treated implantable lead samples were prepared by coating the inside and outside polyurethane surfaces thereof with a copolymer surface graft prepared from acrylic acid and acrylamide monomer. The copolymer surface graft had an acrylic acid/acrylamide copolymer ratio of 3:1, thus fraction acrylic acid was 75%. The surface graft matrix was loaded with gentamicin by an immersion process (see for example EXAMPLE 2).

Lead sample implants were performed in rats. Bacterial inoculation took place at the time of implantation. In a comparative study, the in vivo performance of these lead samples was compared with that of control lead samples, lead samples that were filled with an aqueous solution of gentamicin sulfate, and lead samples that were implanted with a vicinal gentamicin-loaded collagen sponge.
animal model description Male AO-rats of approx. 3 months age were ether-anaesthetized. At the side of the shaved and disinfected back of the rat, an incision of ±1 cm was made in the skin and a subcutaneous pocket was created parallel to the spine. The syringe with the lead sample was then inserted in the subcutaneous pocket and the lead sample was pushed out of the syringe, while retracting the latter. Thus the lead sample had been introduced aseptically with the blue wire-end at the incision site. Before closure of the subcutaneous pocket, the implanted lead sample was challenged with bacteria by injection of 10 µl of a bacterial suspension containing approximately $3 \times 10^7$ *Staph. aureus*. Thereafter, the skin was closed with one suture. Two lead samples per rat were subcutaneously implanted on each site of the back.

Lead samples were explanted at day 1, day 2, day 5, day 10, week 3 and week 6 after implantation of the lead sample.

The implant and implant site were evaluated for viable bacteria by moving a cotton swab over the desired spot;

thereafter the cotton swab was contacted with blood-agar plates. The blood-agar plates were incubated for 18 hours at 37° C., followed by counting the bacterial colonies formed. The implant site was evaluated macroscopically as well as microscopically. All implants were carefully dissected from the surrounding tissue. Typically, the explanted specimens were immersion fixed in glutaraldehyde, dehydrated in graded alcohols, and embedded in glycolmethacrylate. Semi-thin sections (2 μm) for light-microscopical evaluations were routinely stained with toluidine blue.

results

As discussed, explanted specimens were evaluated with regard to bacterial counts and histology of the tissue response. The results are summarized in the tables below.

TABLE 3

Rat lead sample study-bacterial cultures

| | control | surface treated | + sponge | + GS sol'n |
|---|---|---|---|---|
| day 1 | o/c/e: numerous | c/p/e: 2 | c/e: few | c: 10; o: numerous |
| day 2 | e + p: 100; c: numerous | negative | o/c: few; p: 40; e: 70 | o/c: few |
| day 5 | o: 200; c/p/e: numerous | negative | negative | negative |
| day 10 | c/p/e: numerous | c/p/e: 10; a: 250 | c/p/e: numerous | negative |
| wk 3 | c/p/e: numerous | negative | c/p/e: numerous | negative |
| wk 6 | - (abscess removed) | negative | c/p/e: few | c/p/e: few | explanation to abbreviations (see also FIG. 9)
  o=outside tissue encapsulation
  c=tissue capsule
  p=polyurethane
  e=electrode/blue wire
  a=abscess The results demonstrate the superior performance of the surface treated lead samples in fighting the infectious challenge. The summarized results in the following tables show that they were not only the most effective in complete kill of the inoculated bacteria, they also demonstrated to induce a better tissue response. The latter is of prime importance, since it is believed that inappropriate tissue regeneration and healing facilitates the establishment of (secondary) infectious complications.

TABLE 4

Rat lead sample study-macroscopic evaluation

| | control | surface treated | + sponge | + GS sol'n |
|---|---|---|---|---|
| day 1 | inflamed "glassy" capsule | lightly infectious | non-infectious | non-infectious |
| day 2 | heavily infected; intense inflammation; pus | "glassy" capsule | clearly infected inflamed tissue | inflamed tissue |
| day 5 | heavily infected; thick encapsulation; strong inflammation | quiet response | infectious; inflammation; wound fluid/ pus; thick capsule | infectious; inflammation; wound fluid/ pus; thick capsule |
| day 10 | fistula near skin; abscess | infectious; small firm abscess; "glassy" capsule | several abscesses | quiet response; thin capsule |
| wk 3 | thick inflamed capsule | thin capsule | thick capsule; clear inflammation | some inflammation |
| wk 6 | fistula; removed abscess | thin capsule | thin capsule | thin capsule |

TABLE 5

Rat Lead sample study-histological evaluation

| | control | surface treated | + sponge | + GS sol'n |
|---|---|---|---|---|
| day 1 | neutrophils, fibrin, eosinophils (degranulating) | neutrophils, fibrin, wound fluid | eosinophils, fibrin, neutrophils, mast cells | fibrin, neutrophils, eosinophils, mast cells; cells with bacterial inclusions |
| day 2 | large abscess containing many bacteria, fibrin, neutrophils | neutrophils, fibrin, wound fluid | small compact abscess | medium sized compact abscess |
| day 5 | intense infection; hemorrhages, fibrin, neutrophils, many bacteria | normal morphology of adhering cells (macrophages); few granulocytes and eosinophils | accumulations of proteinaceous material/pus | accumulations of proteinaceous material/pus |
| day 10 | many bacteria, neutrophils, few lymphocytes; pus around lead, encapsulated by normal cell layers | abscesses; some lymphocytes and eosinophils | abscess-like morphology around sponge with degenerating fibroblasts | quiet encapsulation; lymphocyte infiltration |
| wk 3 | thick capsule of abscess-like | very quiet capsule; few remnant signs | thick capsule with first layer | small, quiet capsule; |

TABLE 5-continued

Rat Lead sample study-histological evaluation

|   | control | surface treated | + sponge | + GS sol'n |
|---|---------|-----------------|----------|------------|
|   | morphology | of infection | containing many neutrophils; abscess at electrode | remnant signs of infection |
| wk 6 | thick encapsulation with macrophages/ giant cells | very quiet situation; thin strong capsule | thicker capsule; many phagocytosing cells present | small, quiet capsule; few remnant signs of infection |

13: Whole device implant study—application of technology on Medtronic Lead Model 4300 summary description of implant study

Surface treated conductive leads (Medtronic Lead 4300) were implanted in rabbits and evaluated for efficacy against controls. Bacterial inoculation took place at the time of implantation. Explants were evaluated with regard to bacterial counts and histology of the tissue response.

Surface treated conductive leads were prepared by coating the inside and outside polyurethane surfaces with a copolymer surface graft prepared from acrylic acid and acrylamide monomer. The copolymer surface graft had an acrylic acid/acrylamide copolymer ratio of 3:1, thus fraction acrylic acid was 75%. The surface graft matrix was loaded with gentamicin by an immersion process (see for description EXAMPLE 2).

animal model description

The electrodes were implanted in the M. gracilis, with the small fixation loop sutured to the M. gracilis. The silicone rubber anchoring sleeve was fixed around the electrode with a part of the blue wire. The lead was tunneled under the skin of the belly and side(s) with the connector-end sutured to the subcutis. The electrode was put in a sling under the skin of the groin, to compensate for the length of the electrode.

Bacteria were inoculated near the small fixation loop by injection of 10 $\mu$l of a bacterial suspension containing $\pm 3 \times 10^7$ Staph. aureus. Bacterial inoculation took place at the time of implantation.

Electrodes were explanted at day 4, week 3½, and week 10 after implantation of the electrodes. The implant and implant site were evaluated for viable bacteria by moving a cotton swab over the desired spot; thereafter the cotton swab was contacted with blood-agar plates. The blood-agar plates were incubated for 18 hours at 37° C., followed by counting the bacterial colonies formed.

The implant site was evaluated macroscopically as well as microscopically. All implants were carefully dissected from the surrounding tissue. Typically, the explanted specimens were immersion fixed in glutaraldehyde, dehydrated in graded alcohols, and embedded in glycolmethacrylate. Semi-thin sections (2 $\mu$m) for light-microscope evaluations were routinely stained with toluidine blue.

results

Explanted electrodes were evaluated with regard to bacterial counts and histology of the tissue response. The results are summarized in the tables below.

TABLE 6

Whole device implant study-control devices

| | macroscopic observationas | bacteria cultures | microscopic evaluation/ histology |
|---|---|---|---|
| day 4 | redness, many blood vessels; abscess; spreading of infection along device | 1–2 CFU outside capsule; 200 CFU at muscle site; numerous CFU in lumen | high cellular infiltration and degeneration; granulocytes and bacteria in device's lumen |
| wk 3½ | thick encapsulation; lymph nodes; lumen filled with pus | many CFU at all sites | infectious complications all over; thick capsule with abscess-like structure; lymph nodes with high cellular activity; granulocytes, lymphocytes, macrophages, bacteria, hemorrhages |
| wk 10 | small and firm capsule; several clear abscesses | numerous CFU at all sites | many signs of active infection with a large abscess; many bacterial colonies |

TABLE 7

Whole device implant study-surface treated devices

| | macroscopic observations | bacterial cultures | microscopic evaluation/ histology |
|---|---|---|---|
| day 4 | no redness; no sign of infection; quiet white capsule | all cultures negative except 3 CFU outside capsules | some signs of infection; wound fluid and more cellular infiltration |
| wk 3½ | quiet encapsulation on whole device; transparent wound fluid | all cultures negative | some signs of infection in capsule: macrophages with inclusions |
| wk 10 | no abscesses | all cultures negative | not any sign of infection; very thin capsule |

The results demonstrate the superior performance of the surface treated electrodes in fighting the infectious challenge. While the control electrodes were largely infected, even at 10 weeks post-implantation, the modified electrodes demonstrated a quiet, non-infectious response and a very good tissue integration. As discussed before, the latter is of prime importance, since it is believed that inappropriate tissue regeneration and healing facilitates the establishment of (secondary) infectious complications.

Conclusion

In its most preferred form, surface modification technology has been developed for controlled gentamicin release from an anionic surface graft matrix formed from acrylic acid and acrylamide monomer. The concept involves a copolymer surface graft with a controlled copolymer composition, that releases one hundred percent of the drug in a 3 to 6 weeks time span.

With extensive in vitro evaluation it has been demonstrated the importance of control of the surface graft matrix composition with regard to gentamicin loading and release, and more important with regard to release rate, bactericidal activity and biocompatibility. In in vivo experiments the efficacy of the technology in fighting infectious complications has been demonstrated. Additionally, it has been observed and demonstrated that the surface graft provokes a favorable tissue response.

The preferred surface graft matrix would be composed of an acrylic acid/acrylamide copolymer containing an acrylic acid fraction of 50–75%. Most preferably, the acrylic acid fraction would be in the range of 65–75%. While basically all (poly)cationic drugs can be loaded in this surface graft matrix, the most preferred drug in the scope of this invention is the antimicrobial agent gentamicin.

The polymeric surface of the article or the article per se can be a polyurethane such as a polyether urethane or any of the well known inert biocompatible polymeric materials including polyamides, polycarbonates, polyethers, polyesters, polyolefins, polystyrene, polyurethane, polyvinyl chlorides, silicones, polyethylenes, polypropylenes, polyisoprenes, and polytetrafluoroethylenes. Polyurethane is presently the preferred polymeric substrate in the context of this invention.

Additionally, the substrate material can be a metallic surface, such as titanium, stainless steel or tantalum or any of the well known inert biocompatible metallic materials.

It appears that according to U.S. Pat. No. 5,344,455 positively charged samples can be made using copolymers of APMA and AAM whereas negatively charged samples can be prepared with AMPS. See examples 6 and 7.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

We claim:

1. In a method for making an implantable infection resistant medical electrical lead having a polymeric lead insulator, the insulator providing a cavity with an interior surface surrounding the lead, the improvement comprising:
    providing a graft copolymer on the interior surface of the insulator;
    coupling a bioactive agent to the graft copolymer by contacting the graft copolymer on the interior surface with the bioactive agent; and
    sealing the cavity of the insulator to prevent free movement of body fluid into the cavity.

2. The method of claim 1 wherein the bioactive agent is releasably coupled to the graft copolymer.

3. The method of claim 1 wherein the bioactive agent is an antimicrobial agent.

4. The method of claim 1 wherein the lead insulator has an exterior surface, the improvement further comprising:
    providing a graft copolymer on the exterior surface of the insulator; and
    coupling a bioactive agent to the graft copolymer by contacting the graft copolymer on the exterior surface with the bioactive agent.

5. The method of claim 1 wherein the interior surface is polyurethane.

6. The method of claim 1 wherein the bioactive agent is covalently coupled to the graft copolymer.

7. The method of claim 1 wherein the graft copolymer is provided by polymerizing at least two vinyl functional monomers.

8. The method of claim 7 wherein the vinyl functional monomers comprise acrylamide monomer and a second monomer which has a positive or negative electrical charge.

9. The method of claim 8 wherein the second monomer is acrylic acid.

10. The method of claim 9 wherein acrylic acid is 50–75% of the graft copolymer.

11. The method of claim 10 wherein the bioactive agent is gentamicin.

12. The method of claim 10 wherein acrylic acid is 65–75% of the graft copolymer.

13. The method of claim 12 wherein the bioactive agent is gentamicin.

14. The method of claim 1 wherein coupling is conducted at a pH in the range of about pH 6 to pH 8.

15. The method of claim 2 wherein the graft copolymer provides a charge density on the interior surface, and wherein the bioactive agent is ionically coupled to the graft copolymer.

16. The method of claim 3 wherein the antimicrobial agent is an antibiotic.

17. The method of claim 9 further comprising, prior to providing the graft copolymer on the interior surface of the insulator, a step of determining a ratio of acrylamide to acrylic acid effective to cause sustained release of the bioactive agent from the graft copolymer upon contact with a physiological fluid, the release of the bioactive agent being essentially complete within a predetermined period, and wherein the graft copolymer provided on the interior surface of the insulator comprises acrylamide and acrylic acid in accordance with said ratio.

18. In a method for making an infection-resistant article having at least one biocompatible surface adapted for use in contact with the body or body constituents, blood or blood products the improvement comprising:
    providing a graft copolymer of acrylamide and acrylic acid on the biocompatible surface such that the graft copolymer comprises 50% to 75% acrylic acid; and
    ionically coupling a positively charged antimicrobial agent to the graft copolymer by contacting the graft copolymer on the surface with the antimicrobial agent.

19. The method of claim 18 wherein the graft copolymer comprises 65–75% acrylic acid.

20. The method of claim 18 wherein the biocompatible surface is a polymeric surface.

21. The method of claim 18 wherein the biocompatible surface is a metallic surface.

22. A method for making an infection-resistant article having at least one biocompatible surface adapted for use in contact with the body or body constituents, blood or blood products comprising:
    providing a graft copolymer on the biocompatible surface of the article; and
    ionically coupling a positively charged antimicrobial agent to the graft copolymer by contacting the graft copolymer on the biocompatible surface with the antimicrobial agent;
wherein the graft copolymer comprises acrylamide and acrylic acid in a ratio effective to cause sustained release of the bioactive agent from the graft copolymer during a predetermined period following implantation of the article in a body.

23. The method of claim 21 wherein release of the bioactive agent from the graft copolymer is essentially complete at the end of the predetermined period following implantation of the article.

24. The method of claim 21 wherein the predetermined period is about 3–6 weeks.

25. The method of claim 22 wherein the biocompatible surface is a polymeric surface.

26. The method of claim 22 wherein the biocompatible surface is a metallic surface.

* * * * *